US009463216B2

(12) United States Patent
Krantz et al.

(10) Patent No.: US 9,463,216 B2
(45) Date of Patent: Oct. 11, 2016

(54) POLY-GLUTAMIC ACID ANTI-ANTHRAX COMPOSITIONS AND METHODS FOR USING THE SAME

(71) Applicant: The Regents of the University of California, Oakland, CA (US)

(72) Inventors: Bryan A. Krantz, El Cerrito, CA (US); Alexander F. Kintzer, Berkeley, CA (US); Jakob H. von Moltke, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 794 days.

(21) Appl. No.: 13/738,911

(22) Filed: Jan. 10, 2013

(65) Prior Publication Data

US 2015/0265674 A1 Sep. 24, 2015

Related U.S. Application Data

(60) Provisional application No. 61/585,183, filed on Jan. 10, 2012.

(51) Int. Cl.

*A61K 38/16* (2006.01)
*A61K 47/48* (2006.01)
*A61K 31/198* (2006.01)
*A61K 33/26* (2006.01)

(52) U.S. Cl.

CPC ........... *A61K 38/164* (2013.01); *A61K 31/198* (2013.01); *A61K 33/26* (2013.01); *A61K 47/48315* (2013.01)

(58) Field of Classification Search

None

See application file for complete search history.

(56) References Cited

PUBLICATIONS

Abrami et al., "Anthrax toxin triggers endocytosis of its receptor via a lipid raft-mediated clathrin-dependent process", The Journal of Cell Biology, vol. 160, No. 3, pp. 321-328 (2003).
Ashiuchi et al., "Enzymatic Synthesis of High-Molecular-Mass Poly-γ-Glutamate and Regulation of Its Stereochemistry", Applied and Environmental Microbiology, vol. 70, No. 7, pp. 4249-4255 (2004).
Beall et al., "Rapid Lethal Effect in Rats of a Third Component Found Upon Fractionating the Toxin of Bacillus Anthracis", J. Bacteriol., vol. 83, pp. 1274-1280 (1962).
Brachman et al., "Industrial Inhalation Anthrax", Bacteriological Reviews, vol. 30, No. 3, pp. 646-657 (1966).
Bradley et al., "Identification of the cellular receptor for anthrax toxin", Nature, vol. 414, pp. 225-229 (2001).
Bruckner et al., "Structure of Poly-D-glutamic Acid isolated from Capsulated Strains of B. anthracis", Nature, vol. 172, p. 508-508 (1953).
Cromwick et al., "Effects of manganese (II) on Bacillus licheniformis ATCC 9945A physiology and gamma-poly (glutamic acid) formation", Int. J. Biol. Macromol., vol. 17, No. 5, pp. 259-267 (1995).
Dodd et al., "Functional Comparison of the Two Bacillus anthracis Glutamate Racemases", Journal of Bacteriology, vol. 189, No. 14, pp. 5265-5275 (2007).
Fish et al., "In Vivo-produced Anthrax Toxin", Journal of Bacteriology, vol. 95, No. 3, pp. 919-924 (1968).
Friedlander, Arthur M., "Macrophages Are Sensitive to Anthrax Lethal Toxin through an Acid-dependent Process", The Journal of Biological Chemistry, vol. 261, No. 16, pp. 7123-7126 (1986).
Green et al., "Demonstration of a Capsule Plasmid in Bacillus anthracis", Infection and Immunity, vol. 49, No. 2, pp. 291-297 (1985).
Hoffmaster et al., "Characterization of Bacillus cereus Isolates Associated with Fatal Pneumonias: Strains Are Closely Related to Bacillus anthracis and Harbor B. anthracis Virulence Genes", Journal of Clinical Microbiology, vol. 44, No. 9, pp. 3352-3360 (2006).
Joshi et al., "Synthesis of Potent Inhibitors of Anthrax Toxin Based on Poly-L-Glutamic Acid", Bioconjug. Chem., vol. 17, No. 5, pp. 1265-1269 (2006).
Kintzer et al., "Anthrax toxin protective antigen integrates poly-γ-D-glutamate and pH signals to sense the optimal environment for channel formation", Proc. Natl. Acad. Sci. U.S.A., vol. 109, No. 45, pp. 18378-18383 (2012).
Kintzer et al., "Anthrax Toxin Receptor Drives Protective Antigen Oligomerization and Stabilizes the Heptameric and Octameric Oligomer by a Similar Mechanism", PLoS One, vol. 5, No. 11, pp. e13888 (2010).
Kintzer et al., "Role of the protective antigen octamer in the molecular mechanism of anthrax lethal toxin stabilization in plasma", J. Mol. Biol., vol. 399, No. 5, pp. 741-758 (2010).
Kintzer et al., "The Protective Antigen Component of Anthrax Toxin Forms Functional Octameric Complexes", J. Mol. Biol., vol. 392, No. 3, pp. 614-629 (2009).
Lacy et al., "Structure of heptameric protective antigen bound to an anthrax toxin receptor: A role for receptor in pH-dependent pore formation", Proc. Natl. Acad. Sci. U.S.A., vol. 101, No. 36, pp. 13147-13151 (2004).
Makino et al., "Molecular Characterization and Protein Analysis of the cap Region, Which Is Essential for Encapsulation in Bacillus anthracis", Journal of Bacteriology, vol. 171, No. 2, pp. 722-730 (1989).
Makino et al., Effect of the Lower Molecular Capsule Released from the Cell Surface of Bacillus anthracis on the Pathogenesis of Anthrax, The Journal of Infectious Diseases, vol. 186, pp. 227-233 (2002).
Maurer, Paul H., "Antigenicity of Polypeptides (Poly Alpha Amino Acids)", Journal of Experimental Medicine, vol. 121, pp. 339-349 (1965).
McLean et al., "Metal-Binding Characteristics of the Gamma-Glutamyl Capsular Polymer of Bacillus licheniformis ATCC 9945", Applied and Environmental Microbiology, vol. 56, No. 12, pp. 3671-3677 (1990).
"Notice to Readers: Use of Anthrax Vaccine in Response to Terrorism: Supplemental Recommendations of the Advisory Committee on Immunization Practices", MMWR Morbidity and Mortality Weekly Report, vol. 51, No. 45, pp. 1024-1026 (2002).
Pezard et al., "Contribution of Individual Toxin Components to Virulence of Bacillus anthracis", Infection and Immunity, vol. 59, No. 10, pp. 3472-3477 (1991).

(Continued)

*Primary Examiner* — Thomas S Heard
(74) *Attorney, Agent, or Firm* — Michael B. Rubin; Bozicevic, Field & Francis LLP

(57) ABSTRACT

Methods and compositions for inhibiting entry of an anthrax toxin and/or an anthrax toxin protein into a cell are provided. Aspects of the subject methods include administering to a host an effective amount of poly-γ-Glutamic acid-Fe(III) chelate. Also provided are compositions suitable for use in the subject methods, as well as pharmaceutical preparations thereof.

9 Claims, 4 Drawing Sheets

(56) References Cited

PUBLICATIONS

Sanda et al., "Chemical Synthesis of Poly-γ-glutamic Acid by Polycondensation of γ-Glutamic Acid Dimer: Synthesis and Reaction of Poly-γ-glutamic Acid Methyl Ester", Journal of Polymer Science: Part A: Polymer Chemistry, vol. 39, pp. 732-741 (2001).
Scobie et al., "Human capillary morphogenesis protein 2 functions as an anthrax toxin receptor", Proc. Natl Acad. Sci. U.S.A., vol. 100, No. 9, pp. 5170-5174 (2003).
Scorpio et al., "Poly-γ-Glutamate Capsule-Degrading Enzyme Treatment Enhances Phagocytosis and Killing of Encapsulated Bacillus anthracis", Antimicrobial Agents and Chemotherapy, vol. 51, No. 1, pp. 215-222 (2007).
Sellman et al., "Dominant-Negative Mutants of a Toxin Subunit: An Approach to Therapy of Anthrax", Science, vol. 292, pp. 695-697 (2001).
Stanley et al., "Purification of Factor I and Recognition of a Third Factor of the Anthrax Toxin," J. Gen. Microbiol., vol. 26, pp. 49-66 (1961).
Sue et al. "Capsule Production in Bacillus cereus Strains Associated with Severe Pneumonia", Journal of Clinical Microbiology, vol. 44, No. 9, pp. 3426-3428 (2006).
Troy, Frederic A., "Chemistry and Biosynthesis of the Poly(γ-D-glutamyl) Capsule in Bacillus licheniformis", The Journal of Biological Chemistry, vol. 248, No. 1, pp. 305-315 (1973).
"Update: Investigation of Anthrax Associated with Intentional Exposure and Interim Public Health Guidelines, Oct. 2001", MMWR Morbidity and Mortality Weekly Report, vol. 50, No. 41, pp. 889-893 (2001).
Young et al., "Anthrax Toxin: Receptor Binding, Internalization, Pore Formation, and Translocation", Annu. Rev. Biochem., vol. 76, pp. 243-265 (2007).
Zwartouw et al., "Polyglutamic Acid from Bacillus anthracis Grown in vivo: Structure and Aggressin Activity", Biochemical Journal, vol. 63, No. 3, pp. 437-442 (1956).

POLY-GLUTAMIC ACID ANTI-ANTHRAX COMPOSITIONS AND METHODS FOR USING THE SAME

CROSS-REFERENCE TO RELATED APPLICATION

This application claims the benefit of U.S. Provisional Patent Application No. 61/585,183 filed Jan. 10, 2012, which application is incorporated herein by reference in its entirety.

STATEMENT REGARDING FEDERALLY SPONSORED RESEARCH

This invention was made with Government support under Federal Grant No. R01-AI077703 awarded by the National Institutes of Health. The Government has certain rights in this invention.

INTRODUCTION

Anthrax is an extremely serious disease associated with high morbidity and mortality rates. The disease is caused by the Gram$^+$ bacterium, *Bacillus anthracis*, and is contracted via three principle infection routes: from aerosolized spores through the lungs, skin infections, and gastrointenstinal infections. Only the former produces the most acute form of the disease. In fact, the so-called inhalational form of anthrax is well documented as a deadly disease, where workers in textile mills that processed wool were accidentally exposed to aerosolized micron-sized particles of *B. anthracis* spores embedded in the animal wool. Pathogenic *B. anthracis* secretes two different required virulence factors: anthrax toxin (Atx) and a capsule consisting of poly-γ-D-glutamic acid (γ-DPGA). Atx comprises three nontoxic proteins: protective antigen ($PA_{83}$), hereinafter "PA", is an 83-kDa, cell-binding component that ultimately forms a translocase channel capable of delivering the other two enzyme components, lethal factor (LF) and edema factor (EF), into the cytosol of a host cell. While PA, LF, and EF are individually nontoxic, the combinations of PA+LF or PA+EF create lethal toxin (LT) or edema toxin (ET), respectively; and either combination can cause death.

The particular potency of small numbers of *B. anthracis* spores has been exploited in bioweapons programs, starting around WWII. Although these programs have been discontinued through international treaties, the threat of anthrax attacks remains from non-state terrorist organizations and rogue individuals. Most notably in 2001 a significant attack was launched in the United States using weapon-grade spore powder derived from the Ames strain of *B. anthracis*; the powder was delivered to various targets using the US postal system.

In developed countries, occurrences of the disease in wild and livestock herbivores have been minimized through animal vaccination programs. The vaccine used today is largely based on that originally produced by Pasteur. However, human immunization programs are not widespread and generally restricted to military personnel, because the vaccine has side effects. Moreover, some reports indicate that the vaccine may not be effective against the inhalational form of the disease. Other therapies have been developed to deal with exposures to the spores, namely courses of antibiotics, such as Ciprofloxacin, and specific anti-PA antibody treatments. Another method employs a decoy PA protein that acts as a dominant negative inhibitor. Some of these therapies can be effective, but they have several drawbacks, in addition to side effects and cost constraints. While antibiotics may be able to clear anthrax infection in cases where the bacterium does not carry a resistance gene, the Atx protein factors may remain and continue to afflict the patient with serious anthrax symptoms. Furthermore, specific anti-PA antibodies are challenging to produce in large quantities and store. Dominant-negative PA inhibitors have suffered from lipopolysaccharide contamination and side effects in initial trials. Therefore, there remains a significant need to develop cheap, effective countermeasures to anthrax toxin.

For anthrax toxin to achieve cytotoxicity, PA, LF, and EF must first self-assemble into holotoxin complexes. In one possible assembly mechanism, PA first binds to one of two known anthrax toxin receptors (ANTXRs), where it is cleaved by a furin-type protease, and then assembles into a mixture of receptor-bound heptameric and octameric oligomers. The complexes are endocytosed and brought to an acidic compartment, where PA oligomers then transform into transmembrane translocase channels, allowing the passage of LF and EF into the cytosol. A second assembly mechanism has been suggested to occur in the host bloodstream, whereby proteolytic activation of PA by a serum protease allows assembly in the presence of LF or EF, producing LT or ET, respectively.

Virulent strains of *B. anthracis* also produce a second virulence factor, the poly-γ-D-glutamic acid (γ-DPGA) capsule, which is comprised of a long, linear polypeptide (50 to 200 kDa) that is polymerized via amide bonds between the γ-carboxylate side chain of one D-Glu and the α-amino group of adjacent D-Glu (FIG. 1A). These γ-DPGA chains are synthesized and secreted by a non-ribosomal pathway that was initially characterized in *B. licheniformis*. The genes responsible for producing γ-DPGA, anchoring it to the peptidoglycan cell wall, and cleaving it into smaller (15 to 50 kDa), dissociable fragments, may augment its virulence by allowing the *bacillus* to resist complementation and phagocytosis. Indeed, strains deficient for the pXO2 plasmid, the plasmid that is responsible for encoding the γ-DPGA biosynthetic enzymes and secretory machinery, are avirulent. The acquisition of genes responsible for γ-DPGA biosynthesis in several strains of *Bacillus cereus* has been linked to its virulence and pathogenicity. The γ-DPGA purified from *B. anthracis* possesses a unique configuration from most other bacilli; it is exclusively composed of D-Glu (FIG. 1, Panel A). Two racemases maintain the chiral homogeneity of γ-DPGA in *B. anthracis*; and notably, these racemases are not conserved in other species. Many bacilli have significantly racemized, poly-γ-glutamic acid capsules (γ-DLPGA). In *Bacillus licheniformis*, extracellular metal ions may regulate the racemic composition of the γ-DLPGA; the capsule is composed of −90% D-Glu in the presence of high concentrations of Mn(II) but ~25-50% D-Glu in the absence of Mn(II), where the balance is the L-Glu isomer. The significance of these changes in chirality is not well understood.

SUMMARY

Methods and compositions for inhibiting entry of an anthrax toxin and/or an anthrax toxin protein into a cell and modulating an anthrax toxin mediated disease condition in a host are provided. Aspects of the subject methods include administering to a host an effective amount of poly-γ-Glutamic acid-Fe(III) chelate. Also provided are compositions suitable for use in the subject methods, as well as pharmaceutical preparations thereof.

DETAILED DESCRIPTION

Figure 1:
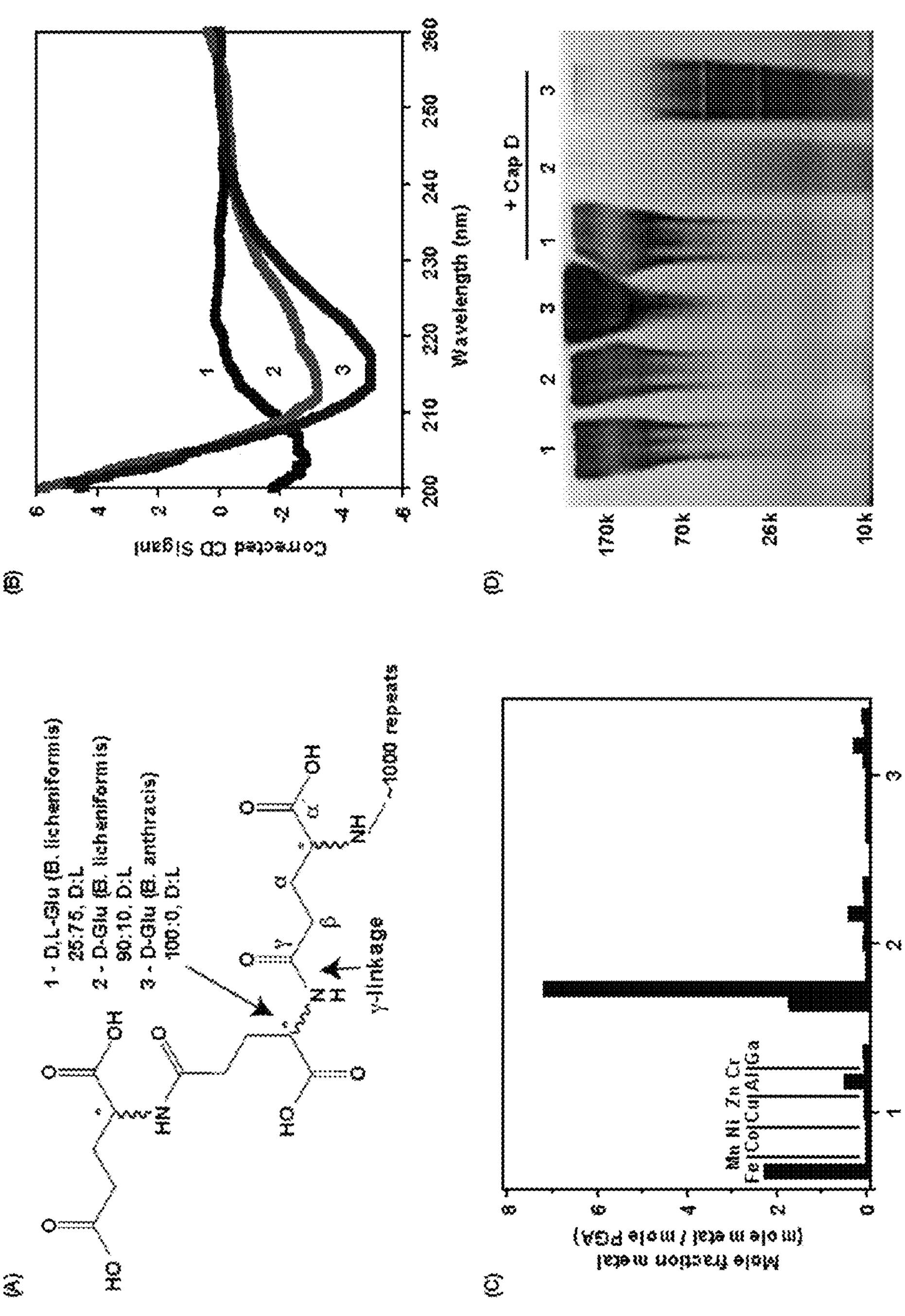
FIG. 1: Structure and composition of γ-DPGA and γ-DLPGA. (Panel A) Schematic diagram of the γ-DPGA or γ-DLPGA component of the *B. licheniformis* and *B. anthracis* capsules. These Glu polymers are linked via the side chain γ-carboxyl to the main chain amino group of the adjacent monomer. Unprocessed polymers are of various lengths, ranging from 200-400 kDa. The polymers can vary, however, in the degree of racemization of the Glu residues. (Compound 1) γ-DLPGA from *B. licheniformis* is composed of racemic mixtures of D- and L-Glu residues. (Compound 2) γ-DPGA from *B. licheniformis* is composed of −90% D-Glu residues. (Compound 3) γ-DPGA from *B. anthracis* is composed of 100% D-Glu residues. The composition of the γ-DLPGA in *B. licheniformis* can be varied by the metal-ion growth conditions: Compound 1 is obtained from low Mn(II) growth medium, and Compound 2 is obtained from high Mn(II) growth medium. Chiral centers are denoted by stars (*) (Panel B) Circular dichroism (CD) spectra of γ-DLPGA and γ-DPGA samples (Compounds 1, 2, 3). The CD spectra were corrected for concentration by normalizing to the absorbance at 215 nm for each compound (CD/Abs215 nm). The CD signal at 215 nm correlates with relative proportions of D-Glu amino acid content, as estimated by CD measurements of acid-hydrolyzed samples. (Panel C) Compounds 1, 2, and 3 can bind Fe(III), Mn(II) and other metal ions. The order of metal ions shown from left to right for Compound 1 is the same for Compounds 2 and 3. The mole fractions of bound metal ions per polymer were measured by inductively coupled plasma atomic emission spectroscopy (ICP-AES). (Panel D) A methylene blue-stained SDS-PAGE gel of Compounds 1, 2, and 3 that were subjected to proteolysis by the *B. anthracis*, γ-DPGA-specific protease, Cap D. Molecular weights are indicated based on protein standards.

Methods and compositions for inhibiting entry of an anthrax toxin and/or an anthrax toxin protein into a cell, as well as methods of modulating an anthrax toxin mediated disease condition in a host are provided. Aspects of the subject methods include administering to a host an effective amount of poly-γ-Glutamic acid-Fe(III) chelate. Also provided are compositions suitable for use in the subject methods, as well as pharmaceutical preparations thereof.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the subject invention, a more detailed review of embodiments of the methods is first provided, followed by a review of embodiments of utilities in which the methods find use and embodiments of compositions that find use in the methods.

Methods

Aspects of the invention include methods of inhibiting entry of anthrax toxin and/or an anthrax toxin protein into a cell. By inhibiting anthrax toxin and/or anthrax toxin protein entry into a cell is meant that the amount of anthrax toxin and/or an anthrax toxin protein that enters a cell, as measured using any convenient protocol, is decreased by an amount of 2-fold or more, usually by 5-fold or more and including by 25-, 50-, 100-fold or more, as compared to a control, i.e., a cell that is not subjected to the methods of the present invention. In certain embodiments, the methods are methods of inhibiting entry of anthrax toxin and/or an anthrax toxin protein into a cell, such that the cell does not die upon exposure of the cell to anthrax toxin.

The anthrax toxin protein whose entry into a cell is inhibited via the subject methods is one that is produced by *B. anthracis*. In certain embodiments, the anthrax toxin protein of interest is one or more of protective antigen (PA), lethal factor (LF) and edema factor (EF). In certain embodiments, the methods result in a decreased presence, e.g., of free cytosolic LF and/or EF in the cell cytosol following exposure of the cell to *B. anthracis*, as compared to a control (e.g., by an amount of 2-fold or more, usually by 5-fold or more and including by 25-, 50-, 100-fold or more).

Aspects of the invention include contacting a cell with an effective amount poly-γ-Glutamic acid-Fe(III) chelate that inhibits anthrax toxin and/or an anthrax toxin protein entry into the cell. In certain embodiments, the poly-γ-Glutamic acid-Fe(III) chelate is one that inhibits anthrax toxin and/or anthrax toxin protein entry mediated by a cell surface protein, such as a protein of the cell having an extracellular domain. In certain embodiments, the poly-γ-Glutamic acid-Fe(III) chelate inhibits ANTXR2-mediated cellular entrance or internalization.

Suitable poly-γ-Glutamic acid-Fe(III) chelates include, for example, poly-γ-D-Glutamic acid-Fe(III) chelates and poly-γ-DL-Glutamic acid-Fe(III) chelates. In some embodiments, the poly-γ-Glutamic acid of the poly-γ-Glutamic acid-Fe(III) chelate has a molecular weight of from about 200 kDa to about 400 kDa, e.g., from about 250 kDa to about 350 kDa. In some embodiments, the poly-γ-Glutamic acid of the poly-γ-Glutamic acid-Fe(III) chelate has a molecular weight of from about 200 kDa to about 220 kDa, from about 220 kDa to about 240 kDa, from about 240 kDa to about 260 kDa, from about 260 kDa to about 280 kDa, from about 280 kDa to about 300 kDa, from about 300 kDa to about 320 kDa, from about 320 kDa to about 340 kDa, from about 340 kDa to about 360 kDa, from about 360 kDa to about 380 kDa, or from about 380 kDa to about 400 kDa.

Where the poly-γ-Glutamic acid-Fe(III) chelate is a poly-γ-DL-Glutamic acid-Fe(III) chelate, the poly-γ-DL-Glutamic acid-Fe(III) chelate may include from about 25% to about 90% D-Glutamic acid and about 75% to about 10% L-Glutamic acid, e.g., from about 30% to about 85% D-Glutamic acid and about 70% to about 15% L-Glutamic acid, from about 35% to about 80% D-Glutamic acid and about 65% to about 20% L-Glutamic acid, from about 40% to about 75% D-Glutamic acid and about 60% to about 25% L-Glutamic acid, from about 45% to about 70% D-Glutamic acid and about 55% to about 30% L-Glutamic acid, from about 50% to about 65% D-Glutamic acid and about 50% to about 35% L-Glutamic acid, from about 55% to about 60% D-Glutamic acid and about 45% to about 40% L-Glutamic acid.

Each poly-γ-Glutamic acid-Fe(III) chelate may include, for example, from about 3 to about 5 Fe(III) atoms.

In some embodiments, the poly-γ-DL-Glutamic acid-Fe(III) chelate is resistant to digestion by *B. anthracis* γ-DPGA depolymerase enzyme (CapD), for example, where the poly-γ-DL-Glutamic acid-Fe(III) chelate comprises about 25% D-Glutamic acid and about 75% L-Glutamic acid, the poly-γ-DL-Glutamic acid-Fe(III) chelate is resistant to digestion by CapD.

Contact of the cell with the poly-γ-Glutamic acid-Fe(III) chelate may occur using any convenient protocol. The protocol may provide for in vitro or in vivo contact of the poly-γ-Glutamic acid-Fe(III) chelate with the target cell, depending on the location of the target cell. Contact may or may not include entry of the poly-γ-Glutamic acid-Fe(III) chelate into the cell.

Where the target cell or cells are part of a multicellular organism, the poly-γ-Glutamic acid-Fe(III) chelate may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body.

A suitable subject for administration of a poly-γ-Glutamic acid-Fe(III) chelate according to the present disclosure may include, e.g., a subject who has been identified as suffering from a disease condition caused by *B. anthracis*, an anthrax toxin and/or an anthrax toxin protein. Suitable subjects may also include individuals identified as having been exposed to or having a risk of being exposed to *B. anthracis*, an anthrax toxin and/or an anthrax toxin protein.

In the subject methods, the poly-γ-Glutamic acid-Fe(III) chelate may be administered to the targeted cells using any convenient means capable of resulting in the desired activity. Thus, the poly-γ-Glutamic acid-Fe(III) chelate (also referred to herein as the agent) can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the poly-γ-Glutamic acid-Fe(III) chelate may be used alone or in appropriate association, as well as in combination, with other pharmaceutically active agents. The following methods and excipients are merely exemplary and are in no way limiting.

For oral preparations, the poly-γ-Glutamic acid-Fe(III) chelate can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The poly-γ-Glutamic acid-Fe(III) chelate can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The poly-γ-Glutamic acid-Fe(III) chelate can be utilized in aerosol formulation to be administered via inhalation. The agents of the present invention can be formulated into pressurized acceptable propellants such as dichlorodifluoromethane, propane, nitrogen and the like.

Furthermore, the poly-γ-Glutamic acid-Fe(III) chelate can be made into suppositories by mixing with a variety of bases such as emulsifying bases or water-soluble bases. The agents of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier. The term "unit dosage form," as used herein, refers to physically discrete units suitable as unitary dosages for human and animal subjects, each unit containing a predetermined quantity of the agent of the present invention calculated in an amount sufficient to produce the desired effect in association with a pharmaceutically acceptable diluent, carrier or vehicle. The specifications for the novel unit dosage forms of the present invention depend on the particular agent employed and the effect to be achieved, and the pharmacodynamics associated with each compound in the host.

In some embodiments, the amount of poly-γ-Glutamic acid-Fe(III) chelate provided in a formulation according to the present disclosure, e.g., a unit dosage form according to the present disclosure, is from about 1 μg to about 10 g, e.g., from about 1 μg to about 100 μg, from about 100 μg to about 500 μg, from about 500 μg to about 1 mg, from about 1 mg to about 100 mg, from about 100 mg to about 500 mg, from about 500 mg to about 1 g, or from about 1 g to about 10 g.

In some embodiments, a formulation according to the present disclosure, including a poly-γ-Glutamic acid-Fe(III) chelate, e.g., a unit dosage form, includes an amount of Fe(III) which is less than 10 mM, e.g., an amount of Fe(III) which is less than 10 mM and greater than or equal to about 1 μM, an amount of Fe(III) which is less than or equal to about 5 mM and greater than or equal to about 1 μM, an amount of Fe(III) which is less than or equal to about 1 mM and greater than or equal to about 1 μM, an amount of Fe(III) which is less than or equal to about 100 μM and greater than or equal to about 1 μM, or an amount of Fe(III) which is less than or equal to about 50 μM and greater than or equal to about 1 μM.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels can vary as a function of the specific agent, the nature of the delivery vehicle, and the like. Preferred dosages for a given agent are readily determinable by those of skill in the art by a variety of means.

As reviewed above, the subject methods result in inhibition of anthrax toxin and/or anthrax toxin protein entry into a target cell or cells, where the target cell(s) may be in vitro or in vivo. In certain embodiments, the subject methods result in inhibition of anthrax toxin and/or anthrax toxin protein entry into a target cell(s). In certain embodiments, the methods result in a reduction of anthrax toxin susceptibility of a cell, e.g., as measured using the assay protocols described in the experimental section below.

The above methods find use in a variety of different applications. Certain applications are now reviewed in the following Utility section.

Utility

The methods find use in a variety of therapeutic applications in which it is desired to decrease anthrax toxin and/or anthrax toxin protein entry into a target cell or collection of cells, where the collection of cells may be a whole animal or portion thereof, e.g., tissue, organ, etc. In such methods, an effective amount of poly-γ-Glutamic acid-Fe(III) chelate is administered to the target cell or cells, e.g., by contacting the cells with the poly-γ-Glutamic acid-Fe(III) chelate, by administering the poly-γ-Glutamic acid-Fe(III) chelate to the animal, etc. By effective amount is meant a dosage sufficient to modulate anthrax toxin and/or anthrax toxin protein entry into the cell, as desired.

For example, an effective amount of a poly-γ-Glutamic acid-Fe(III) chelate may be from about 1 μg to about 10 g, e.g., from about 1 μg to about 100 μg, from about 100 μg to about 500 μg, from about 500 μg to about 1 mg, from about 1 mg to about 100 mg, from about 100 mg to about 500 mg, from about 500 mg to about 1 g, or from about 1 g to about 10 g.

In some embodiments, e.g., when administering to an animal, e.g., a human, an effective amount may be from about 100 μg/kg body weight to about 50 mg/kg body weight, e.g., from about 100 μg/kg to about 500 μg/kg, from about 500 μg/kg to about 1 mg/kg, from about 1 mg/kg to about 10 mg/kg or from about 10 mg/kg to about 50 mg/kg. The subject methods find use in the treatment of a variety of different conditions in which the decrease of anthrax toxin and/or anthrax toxin protein cell entry is desired. In representative embodiments, the methods are employed to treat an anthrax toxin mediated condition in a subject. In certain of these embodiments, the methods are methods of prophylactically conferring an anthrax toxin resistant phenotype on the subject, such that the subject can later be exposed to *B. anthracis* and not suffer from subsequent anthrax toxin mediated disease conditions. In certain embodiments, the methods are employed to treat a subject suffering from an anthrax mediated disease condition resulting from exposure to *B. anthracis*. In certain of these embodiments, the methods include first diagnosing the presence of such a condition in the subject. By treatment is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition. In certain of the embodiments, the subject methods find use in the treatment of host having a "late-stage" disease condition, where a substantial amount of anthrax toxin is present in the host and the condition is no longer treatable by targeting the pathogen itself.

The subject methods are useful for both prophylactic and therapeutic purposes. Thus, as used herein, the term "treating" is used to refer to both prevention of disease and treatment of a pre-existing condition.

A "subject" or "patient" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Pharmaceutical Preparations

Also provided are pharmaceutical preparations of the subject agents. The subject agents can be incorporated into a variety of formulations for administration to a subject. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. The formulations may be designed for administration via a number of different routes, including oral, buccal, rectal, parenteral, intraperitoneal, intradermal, transdermal, intracheal, etc., administration.

In pharmaceutical dosage forms, the agents may be used alone or in appropriate association, as well as in combination, with other pharmaceutically active agents. The following methods and excipients are merely exemplary and are in no way limiting.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874; the disclosures of each of which are incorporated by reference herein; to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The agents of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The agents of the present invention can be administered rectally via a suppository. The suppository can include vehicles such as cocoa butter, carbowaxes and polyethylene glycols, which melt at body temperature, yet are solidified at room temperature.

To the extent the agents of the invention are active for topical administration, they can be formulated as transdermal compositions or transdermal delivery devices ("patches"). Such compositions include, for example, a backing, active agent reservoir, a control membrane, liner and contact adhesive. Such transdermal patches may be used to provide continuous or discontinuous infusion of the agents of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference in its entirety. Such patches may be constructed for continuous, pulsatile, or on demand delivery of pharmaceutical agents.

Optionally, the pharmaceutical composition may contain other pharmaceutically acceptable components, such a buffers, surfactants, antioxidants, viscosity modifying agents, preservatives and the like. Each of these components is well-known in the art. See, for example, U.S. Pat. No. 5,985,310, the disclosure of which is herein incorporated by reference.

Other components suitable for use in the formulations of the present invention can be found in Remington's Pharmaceutical Sciences, Mace Publishing Company, Philadelphia, Pa., 17th ed. (1985), the disclosure of which is incorporated herein by reference. In an embodiment, an aqueous cyclodextrin solution which includes dextrose, e.g., about 5% dextrose, may be utilized.

The amount of poly-γ-Glutamic acid-Fe(III) chelate that may be combined with the carrier materials to produce a single dosage form will vary depending upon the host treated and the particular mode of administration. The specific dose level for any particular patient will depend upon a variety of factors including the age, body weight, general health, sex, diet, time of administration, route of administration, rate of excretion, drug combination and the severity of the particular disease undergoing therapy.

In some embodiments, the amount of poly-γ-Glutamic acid-Fe(III) chelate provided in a pharmaceutical formulation according to the present disclosure, e.g., a unit dosage form according to the present disclosure, is from about 1 μg to about 10 g, e.g., from about 1 μg to about 100 μg, from about 100 μg to about 500 μg, from about 500 μg to about 1 mg, from about 1 mg to about 100 mg, from about 100 mg to about 500 mg, from about 500 mg to about 1 g, or from about 1 g to about 10 g.

In some embodiments, a pharmaceutical formulation according to the present disclosure, including a poly-γ-Glutamic acid-Fe(III) chelate, e.g., a unit dosage form, includes an amount of Fe(III) which is less than 10 mM, e.g., an amount of Fe(III) which is less than 10 mM and greater than or equal to about 1 μM, an amount of Fe(III) which is less than or equal to about 5 mM and greater than or equal to about 1 μM, an amount of Fe(III) which is less than or equal to about 1 mM and greater than or equal to about 1 μM, an amount of Fe(III) which is less than or equal to about 100 μM and greater than or equal to about 1 μM, or an amount of Fe(III) which is less than or equal to about 50 μM and greater than or equal to about 1 μM.

As such, unit dosage forms for oral or rectal administration such as syrups, elixirs, and suspensions may be provided wherein each dosage unit, for example, teaspoonful, tablespoonful, tablet or suppository, contains a predetermined amount of the composition containing the poly-γ-Glutamic acid-Fe(III) chelate. Similarly, unit dosage forms for injection or intravenous administration may comprise the poly-γ-Glutamic acid-Fe(III) chelate in a composition as a solution in sterile water, normal saline or another pharmaceutically acceptable carrier.

Kits

Kits with unit doses of the agents, such as in oral or injectable doses, are provided. For example, kits and systems for practicing the subject methods may include one or more pharmaceutical formulations.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Methods of Making Poly-γ-Glutamic Acid-Fe(III) Chelates

The present disclosure provides methods of making poly-γ-Glutamic acid-Fe(III) chelates as described herein for use in the disclosed methods and compositions. For example, poly-γ-Glutamic acid-Fe(III) chelates may be produced via bacterial fermentation or the utilization of synthetic chemistry techniques. In the case of bacterial fermentation, bacterial species, growth conditions and media composition may be selected so as to provide a desired level of metal ion incorporation into the chelates and/or desired D-Glu:L-Glu ratio. For example, the composition of the γ-DLPGA produced by *B. licheniformis* can be varied by varying the metal-ion growth conditions as described herein, e.g., by adjusting the Mn(II) level in the growth medium. These parameters may be selected, for example, so as to provide a poly-γ-DL-Glutamic acid-Fe(III) chelate including about 25% to about 90% D-Glutamic acid and about 75% to about 10% L-Glutamic acid.

In some embodiments, a method of making a poly-γ-Glutamic acid-Fe(III) chelate is provided which includes combining Fe(III) with an isolated poly-γ-Glutamic acid, e.g, a poly-γ-D-Glutamic acid or a poly-γ-DL-Glutamic acid. The poly-γ-Glutamic acid will bind the Fe(III), forming a chelate. Poly-γ-Glutamic acids for use in such methods may be produced synthetically, e.g., as described in Sanda et al. *Journal of Polymer Science*, (2001) Vol. 39, 5: 732-741, or isolated from bacteria, e.g., as described in Sung et al. *Chem. Rec.* (2005) 5(6):352-66, the disclosures of each of which are incorporated by reference herein.

The following examples are offered by way of illustration and not by way of limitation.

EXPERIMENTAL

It is demonstrated herein that γ-DPGA and γ-DLPGA purified from *B. anthracis* and *B. licheniformis* can form a complex with PA, which can completely inhibit the toxin in approximately a one-to-one binding stoichiometry. While the γ-DPGA obtained from these sources has been shown to be free of contaminants, the structural homogeneity was confirmed as described herein by a variety of independent methods. Sodium dodecylsulfate polyacrylamide gel electrophoresis (SDS-PAGE) showed that no other protein components, which stain with Coomassie Brilliant Blue, were present in the sample. γ-DPGA and γ-DLPGA are only stained by methylene blue, and the purified polymers ran as a 200-400 kDa band on native PAGE (FIG. 1, Panel D). The purified γ-DPGA and γ-DLPGA polymers were resistant to DNAse, RNAase, and protease digestion by bromelain, trypsin, and proteinase K. However, the γ-DPGAs with ~100% and –89% D-Glucose, but not γ-DLPGA with ~24% D-Glucose, were readily digested by the specific *B. anthracis* γ-DPGA depolymerase enzyme, CapD, which was obtained from recombinant overexpression in *E. coli* (FIG. 1, Panel D). $^{1}H$ and $^{13}C$ NMR confirmed the Glu content and γ-linkage. Thin-layer chromatography of hydrolyzed γ-DPGA alongside amino acid standards confirmed that these samples were composed exclusively of Glu residues. The chirality differences between the PGA material isolated from *B. anthracis* and *B. licheniformis* has been confirmed by circular dichroism (CD) (FIG. 1, Panel B). The most racemic γ-DLPGA (~24% D-Glu, compound 1) possessed little CD signal at 215 nm relative to the less racemic γ-DPGA (~89% D-Glu, compound 2), where the γ-DPGA from *B. anthracis* (compound 3) possessed the greatest CD signal at 215 nm consistent with its uniform D-Glu composition. CD measurements of acid-hydrolyzed monomers of compounds 1, 2, and 3 enabled the calculation of D-Glu content, based on standard curves of known D- and L-Glu compositions. Compounds 1, 2, and 3 were determined to have 24.1±1%, 89.4±4%, and 93.9±4% D-glutamic acid, respectively.

Since these compounds are composed of poly-carboxylates, which have known metal ion chelation activities, the metal ion species that naturally associate with the polymers during their isolation were analyzed as described herein. Using inductively coupled plasma atomic emission spectroscopy (ICP-AES), significant concentrations of Mn(II) and Fe(III) were measured in the samples from *B. licheniformis* (FIG. 1, Panel C). Each polymer contains ~3-5 atoms of these divalent metal ions depending on the composition of the medium. γ-DLPGA (compound 1) harvested from low Mn(II) medium contained the same levels of Fe(III) but had diminished Mn(II) levels relative to the γ-DPGA (compound 2) grown in high Mn(II). γ-DPGA (compound 3) purified from *B. anthracis* was devoid of metals, owing to the necessary autoclave sterilization procedure and trichloroacetic acid treatments (used for biosafety purposes).

γ-DPGA (compounds 2 and 3) and γ-DLPGA (compound 1) chelates were tested to determine whether they could bind to PA and affect its activity. In vitro blue native PAGE (BN-PAGE) and fluorescence binding assays confirmed that compounds 1, 2, and 3 can form complexes with PA. Interestingly, compound 1 binds PA with 10-fold higher affinity than compound 2. Given the previous studies that have shown that PA must also bind the ANTXR2 receptor to intoxicate cells, the effects of compounds 1, 2, and 3 on LT-uptake and cytotoxicity were tested. Interestingly, it was found that compounds 1 and 2, but not 3, could inhibit LT-mediated cytolysis in bone marrow macrophage cells. Similar results were obtained using the *B. anthracis* Sterne strain as a source of LT. Interestingly, the pretreatment of compound 2 with the γ-DPGA specific enzyme, Cap D, prevents formation of co-complexes with PA and eliminates the stimulation of PA internalization and inhibition of LT-mediated cytotoxicity (FIG. 2B). Compound 1 was not cleavable by Cap D, presumably due to its significant L-Glu content (FIG. 1D). Therefore, cleavage of compound 2 by Cap D, but not compound 1, abolishes inhibitory activity.

Figure 2:
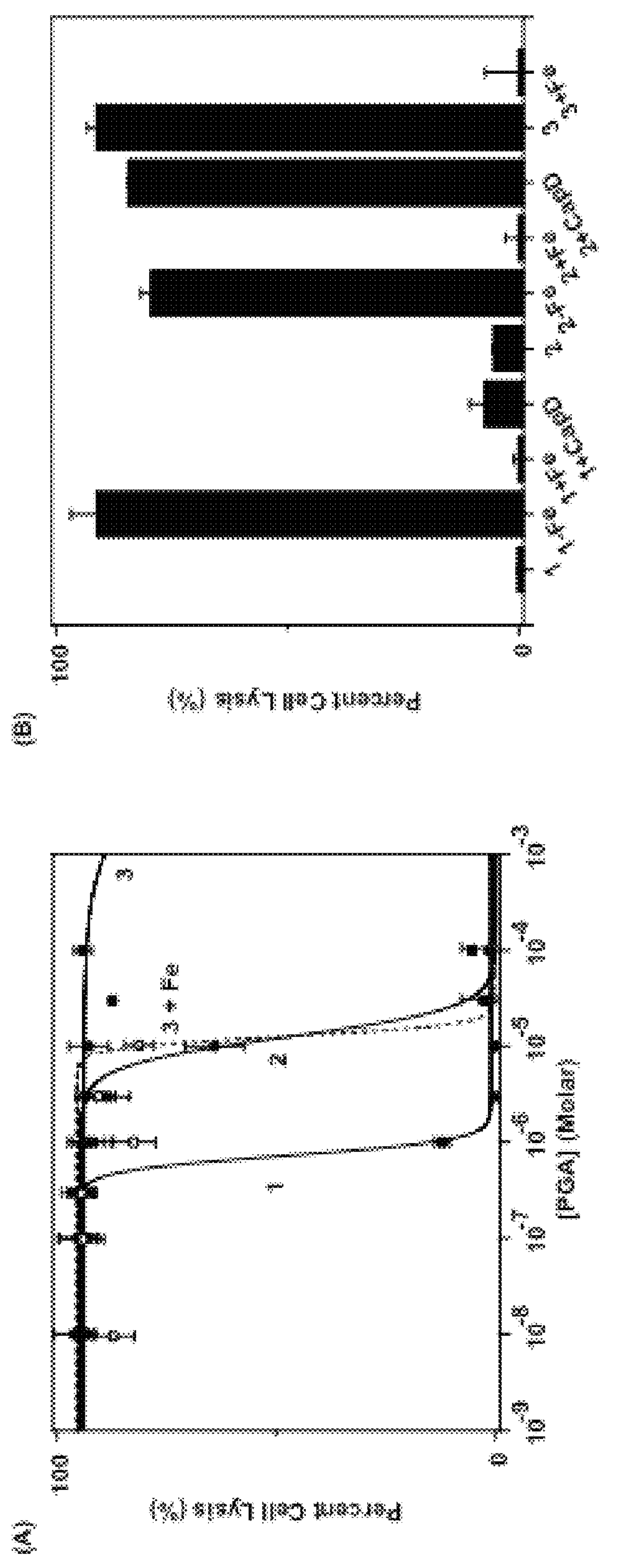
FIG. 2: Inhibition of lethal toxin activity in macrophage cells. Compounds 1, 2, and 3 were titrated with a constant amount of lethal toxin (1 μg/mL PA, 1 μg/mL LF) on bone-marrow macrophage cells. The percent cell lysis was quantified after 4 hours by a lactate dehydrogenase release assay. (Panel A) A plot of the inhibitory activity of compounds 1, 2, and 3. Half-maximal inhibitory values were determined for compounds 1, 2, 3, and 3-Fe(III) complex, to be 0.68±0.07 μM, 12±1 μM, >1 mM, and 12.3±7 μM, respectively. (Panel B) Inhibitory activity of compounds that were natively purified, stripped of metal ions (—Fe), and had Fe(III) added back (+Fe), or treated with Cap D. Percent lysis values are shown for concentrations of 1 μM, 30 μM, and 30 μM for compounds 1, 2, and 3, respectively. Error bars represent the mean plus the standard deviation (n=3).

The role of metal ions in the inhibition mechanism was also investigated. Removing Fe(III) from compounds 1 or 2 by liquid chromatography produced the apo compounds (1-Fe, 2-Fe), as determined by ICP-AES. The apo compounds have 100-1000-fold diminished inhibitory activity (FIG. 2, Panel B). However, when Fe(III) was added back to form compounds 1+Fe(III), 2+Fe(III), and 3+Fe(III), it was possible to fully recover the inhibitory activity (FIG. 2, Panel B). Therefore, the Fe(III) chelates of compound 1, 2, and 3, but not the apo forms of γ-DPGA and γ-DLPGA possess inhibitory activity. Fe(III) alone did not possess inhibitory activity at these concentrations. However, it was found that Fe(III) may inhibit LT, but only at 10 mM concentrations, which are $10^3$-$10^4$-fold greater than the concentrations found to be effective in the Fe(III) co-complexes of compounds 1, 2, and 3. The specificity of compounds 1 and 2 for metal ions was tested. It was found that while compound 1 and 2 could bind Mn(II), Zn(II), Co(II), Ni(II), Cu(II), Zn(II), Al(III), Cr(III), and Ga(III) ions, only the Fe(III) chelate had LT inhibitory activity. Therefore, Fe(III) chelates of compounds 1, 2, and 3 appear to be the most potent inhibitors. While not intending to be bound by any particular theory, it was concluded that the Fe(III) complexes act as an antitoxins by specifically forming an inhibitory complex with PA.

Figure 3:
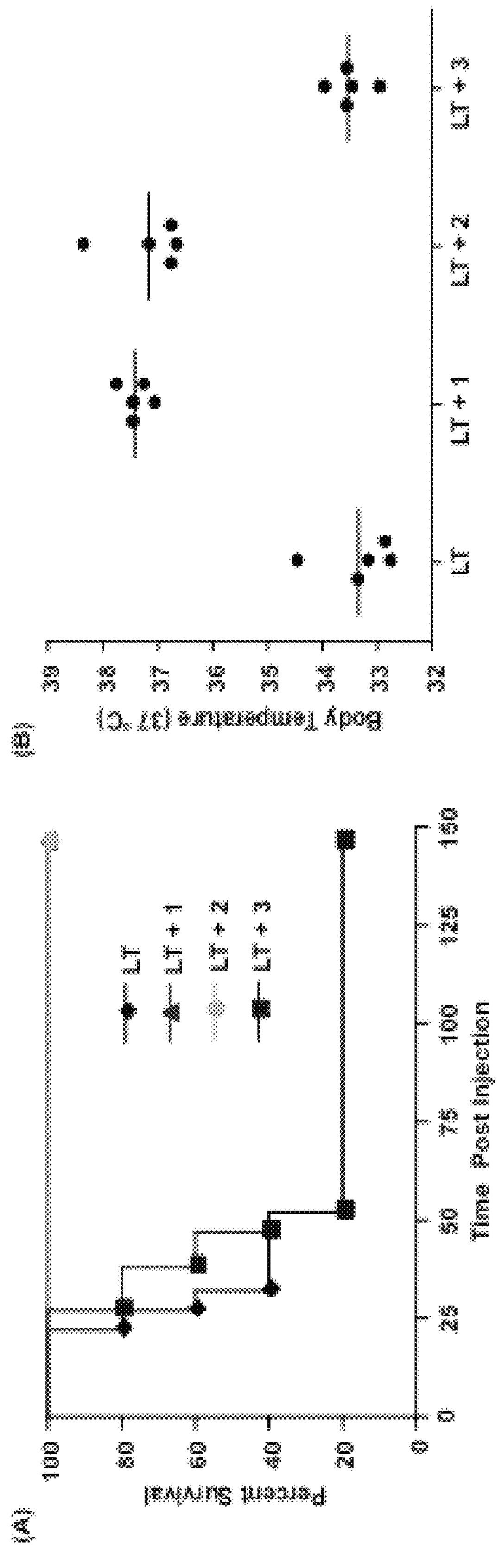
FIG. 3: γ-DPGA-Fe(III) and γ-DLPGA-Fe(III) complexes protect BALB/cJ mice against recombinant LT. A plot of the percent of surviving BALB/cJ (N=5) mice after a challenge with LT and co-injected compounds 1, 2, 3. (Panel A) Purified recombinant LT (100 μg PA+100 μg LF) was co-injected with 100 μg of compound 1, 1 mg of compound 2, and 1 mg of compound 3, and 1 mg of compound 3-Fe(III) complex into 24-25 g BALB/cJ mice (N=5) and the percentage of surviving were monitored every five to eight hours post-injection. In compliance with the standards set by the Animal Care and Use Committee, mice were considered moribund if their body temperature dropped below 26° C.(Panel B) The hypothermic response to LT-uptake is shown. Body temperatures were measured at 1 hour post-infection for the samples described above. At this early time point, a decrease in body temperature to 34° C. indicates the efficient uptake of LT in comparison to normal temperatures at 38° C.

Since compounds 1 and 2 blocked the macrophage cytotoxicity of PA in vitro, it was hypothesized that they may be used as an antitoxin to protect mice from LT. When lethal doses of recombinant LT (100 μg PA, 100 μg LF) were injected in to BALB/cJ mice, it was found that they were completely protected by co-injecting compounds 1 and 2 from *B. licheniformis* (FIG. 3, Panel A). Treatment with Cap D abolished the inhibitory activity of compound 2, which is susceptible to enzymatic cleavage. However, compound 1 is resistant to cleavage, even as an Fe(III) chelate. Compound 3 can be made into an anti-LT inhibitor by pre-complexing the *B. anthracis* γ-DPGA with Fe(III) (FIG. 2), and is reversible by digestion with Cap D. Control compounds such as bovine serum albumin, L-Glu, various α-linked Glu polymers, and buffer did not protect mice from LT.

Figure 4:
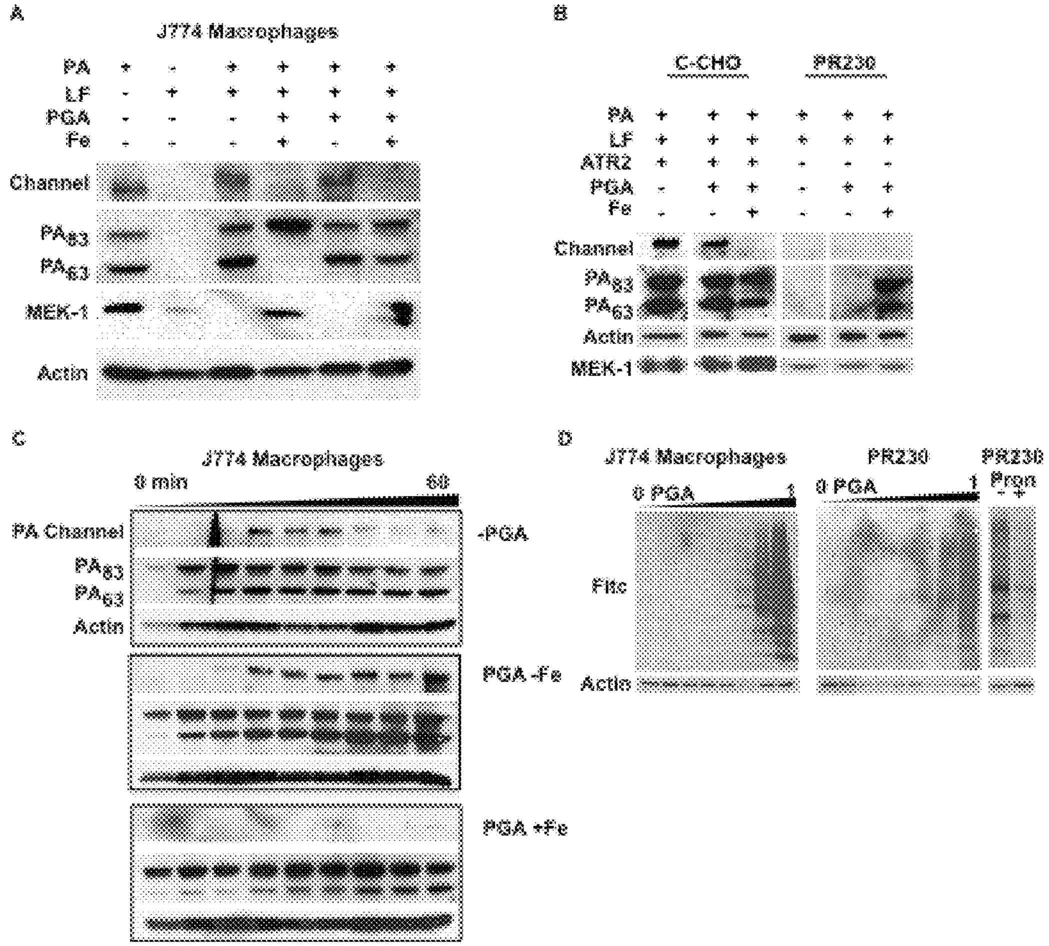
FIG. 4: γ-DPGA reroutes PA uptake through an alternate cell-surface receptor. Western blot analysis of the PA species bound and taken up by (Panel A) J774 macrophages, (Panel B, left) ANXTR2-expressing (CCHO), and (Panel B, right) ANXTR2-null (PR230) chinese hamster ovary cells (CHO) in the presence and absence of LF, γ-DPGA, and γ-DPGA-Fe conjugate. Probes include: PA antibody, which detects intact PA monomers ($PA_{83}$), proteolyzed/assembled PA ($PA_{63}$), and PA channels; MEK-1 is a substrate for LF in the cytosol that reports on translocation; Actin is used as a loading control. (Panel C) Timecourses of PA uptake into J774 macrophages in the (top) absence and presence of (middle) γ-DPGA or (bottom) γ-DPGA-Fe(III) conjugate. (Panel D) Titration of γ-DPGA-Fe(III) conjugates, labeled with fluoroscein isothiocyanate (Fitc), on (left) J774 macrophages and (right) PR230 CHO cells. Lanes represent concentrations of 0, 0.01, 0.03, 0.1, 0.3, and 1 mg/mL γ-DPGA-Fe(III). (Far right) Binding of γ-DPGA-Fe(III) at 1 mg/mL to PR230 cells that were untreated or treated with a minimal amount of Pronase (Pron) to remove cell-surface receptors. The γ-DPGA in detected via an antibody recognizing the Fitc-moiety.

The mechanism of LT inhibition by compounds 1, 2, and 3+Fe was determined as follows. The cytotoxic activity of PA requires precise delivery to the cell-surface ANTXR2 receptor, toxin assembly, followed by ANTXR2-mediated endocytosis, channel formation in the late endosome, and LF translocation to the cytosol. These processes were considered as possible targets of compounds 1, 2, and 3+Fe. The inhibition mechanism is independent of toxin assembly, since PA oligomers are equally inhibited by compounds 1, 2, and 3+Fe. Gel-shift binding assays have shown that compounds 1, 2, and 3+Fe do not affect PA-binding to ANTXR2 or LF, PA oligomerization, or channel formation in vitro. Western blots were then employed to determine the mechanism of compounds 1, 2, and 3+Fe inhibition in J774 macrophages, ANTXR2-expressing (CCHO) and ANTXR2-null (PR230) chinese hamster ovary cells (FIG. 4). It was found that compounds 1, 2, and 3+Fe prevent proper cell uptake by allowing PA to bind cells in an ANTXR2-independent mechanism (FIG. 4, Panel A and Panel B). This new binding mode prevents processing of $PA_{83}$ monomers on the cell surface, which is known to be ANTXR2-dependent (FIG. 4, Panel C). To probe whether compound-mediated cell binding involves a proteinaceous cell-surface receptor, PR230 cells were treated with 0.5 mg/mL Pronase at 4° C., for 30 minutes, washed with media, and titrated with fluoroscein isothiocyanate-labelled (Fitc) compound 2 (FIG. 4D). Binding of compound 2 was probed after incubation for 1 hour at 37° C. and removing the unbound fraction, by analyzing the whole cell lysate by western blot with an antibody against Fitc. While compound 2 binds J774 macrophages and PR230 cells with equal affinity (FIG. 4, panel D), binding to Pronase-treated PR230 cells was significantly reduced, suggesting that a cell-surface protein mediates compound 2 binding to cells.

In view of the above experimental data, it is proposed that γ-DPGA- and γ-DLPGA-Fe(III) conjugates (compound 1, 2, and 3+Fe may be used as a prophylactic treatment for anthrax disease. There are several advantages to this approach: (a) it would be inexpensive to produce, since compounds 1, 2, and 3 could come from the fermentation of bacteria; (b) homo-polymeric compounds 1, 2, and 3 may be readily produced through synthetic chemistry to avoid contamination by bacterial antigens; (c) nontoxic, because compounds 1, 2, and 3 are composed of a natural polypeptide; (d) nonimmunogenic, since compounds 1, 2, and 3 only interact weakly with the innate immune system. Compound 1 may be the most effective treatment, since it is resistant to enzymatic digestion by the CapD enzyme (FIG. 1D). While most antibacterial therapies have associated side effects, side effects from compounds 1, 2, and 3 are unlikely due to their weak immunogenicity. Compounds 1, 2, and 3 may also be administered intravenously.

What is claimed is:

1. A method of inhibiting entry of an anthrax toxin protein into a cell, the method comprising:

contacting the cell with an effective amount of a poly-γ-Glutamic acid-Fe(III) chelate to inhibit entry of the anthrax toxin protein into the cell.

2. The method according to claim 1, wherein the poly-γ-Glutamic acid of the poly-γ-Glutamic acid-Fe(III) chelate has a molecular weight of from about 200 to about 400 kDa.

3. The method according to claim 1, wherein the poly-γ-Glutamic acid-Fe(III) chelate is a poly-γ-D-Glutamic acid-Fe(III) chelate.

4. The method according to claim 1, wherein the poly-γ-Glutamic acid-Fe(III) chelate is a poly-γ-DL-Glutamic acid-Fe(III) chelate.

5. The method according to claim 4, wherein the poly-γ-DL-Glutamic acid-Fe(III) chelate comprises about 25% to about 90% D-Glutamic acid and about 75% to about 10% L-Glutamic acid.

6. The method according to claim 5, wherein the poly-γ-DL-Glutamic acid-Fe(III) chelate comprises about 25% D-Glutamic acid and about 75% L-Glutamic acid, and wherein the poly-γ-DL-Glutamic acid-Fe(III) chelate is resistant to digestion by *B. anthracis* γ-DPGA depolymerase enzyme (CapD).

7. The method according to claim 1, wherein the anthrax toxin protein is selected from lethal factor (LF) and edema factor (EF).

8. The method according to claim 1, wherein the method is in vitro.

9. The method according to claim 1, wherein the method is in vivo.

* * * * *